(12) United States Patent
Mori et al.

(10) Patent No.: US 9,874,532 B2
(45) Date of Patent: Jan. 23, 2018

(54) SCATTER DIAGRAM DISPLAY DEVICE AND SURFACE ANALYZER

(71) Applicant: JEOL Ltd., Tokyo (JP)

(72) Inventors: Norihisa Mori, Tokyo (JP); Masaru Takakura, Tokyo (JP); Shinya Fujita, Tokyo (JP); Shigeru Honda, Tokyo (JP); Naoki Kato, Tokyo (JP); Shuichi Sakamoto, Tokyo (JP)

(73) Assignee: JEOL Ltd., Tokyo (JP)

( * ) Notice: Subject to any disclaimer, the term of this patent is extended or adjusted under 35 U.S.C. 154(b) by 178 days.

(21) Appl. No.: 14/886,345

(22) Filed: Oct. 19, 2015

(65) Prior Publication Data

US 2016/0110896 A1 Apr. 21, 2016

(30) Foreign Application Priority Data

Oct. 20, 2014 (JP) .................. 2014-213657

(51) Int. Cl.
*G06T 11/20* (2006.01)
*G01N 23/225* (2006.01)

(52) U.S. Cl.
CPC .................. *G01N 23/225* (2013.01)

(58) Field of Classification Search
None
See application file for complete search history.

(56) References Cited

U.S. PATENT DOCUMENTS

| 5,596,195 | A  | * | 1/1997  | Obori ............... H01J 37/256 250/305 |
| 9,664,681 | B2 | * | 5/2017  | Imaizumi ......... G01N 33/57423 |
| 2012/0181425 | A1 | * | 7/2012  | Oohashi ............ G01N 23/2251 250/307 |
| 2013/0054603 | A1 | * | 2/2013  | Birdwell ............. G06K 9/6224 707/738 |
| 2013/0173042 | A1 | * | 7/2013  | Morisawa .......... G05B 19/4184 700/121 |
| 2014/0367582 | A1 | * | 12/2014 | Boardman ........... G01V 5/0075 250/395 |
| 2017/0032017 | A1 | * | 2/2017  | Morinaga ............ G06K 9/6247 |

FOREIGN PATENT DOCUMENTS

JP    2011145238 A    7/2011

\* cited by examiner

*Primary Examiner* — Yu Chen
(74) *Attorney, Agent, or Firm* — The Webb Law Firm

(57) ABSTRACT

A scatter diagram display device includes a principal component analysis section that performs principal component analysis on intensity or concentration map data that represents each element, a priority level setting section that sets a priority level to each element based on the results of the principal component analysis performed by the principal component analysis section, and a display control section that performs a control process that arranges a plurality of scatter diagrams generated by combining each element based on the priority level that has been set to each element by the priority level setting section, and displays the plurality of scatter diagrams on a display section.

5 Claims, 9 Drawing Sheets

|  | PRINCIPAL COMPONENT COEFFICIENT OF FIRST PRINCIPAL COMPONENT | PRINCIPAL COMPONENT COEFFICIENT OF SECOND PRINCIPAL COMPONENT |
|---|---|---|
| Al | 2.1 | 1.0 |
| Mg | 0.1 | 2.0 |
| Si | 1.0 | 0.8 |
| Fe | −0.7 | 2.2 |
| Zn | −1.4 | 1.1 |

|  | PRINCIPAL COMPONENT COEFFICIENT OF FIRST PRINCIPAL COMPONENT |
|---|---|
| A l | 2. 1 |
| M g | 2. 1 |
| S i | 0 |
| F e | 0 |
| Z n | 0. 5 |

| SCATTER DIAGRAM | VARIANCE |
|---|---|
| (Al, Mg) | 24 |
| (Al, Si) | 18 |
| (Al, Fe) | 3 |
| (Al, Zn) | 9 |
| (Mg, Si) | 5 |
| (Mg, Fe) | 11 |
| (Mg, Zn) | 1 |
| (Si, Fe) | 2 |
| (Si, Zn) | 16 |
| (Fe, Zn) | 1 |

SCATTER DIAGRAM DISPLAY DEVICE AND SURFACE ANALYZER

Japanese Patent Application No. 2014-213657, filed on Oct. 20, 2014, is hereby incorporated by reference in its entirety.

BACKGROUND OF THE INVENTION

The present invention relates to a scatter diagram display device and a surface analyzer.

Phase analysis has been known as a method for analyzing elemental map data (i.e., detection intensity or concentration distribution data on an element basis) acquired using a surface analyzer such as an electron probe microanalyzer (EPMA). The term "phase analysis" used herein refers to a method that extracts the phase of a compound from the correlation between a plurality of elements, and determines the correlation on a phase basis.

When a number of elements are included in a specimen, the analyst must determine a combination of elements on which the phase analysis should be performed. In this case, a scatter diagram matrix may be generated by arranging a plurality of scatter diagrams generated by combining two different elements in a matrix, and displayed so that the correlation between a plurality of elements can be easily determined (see FIG. 13).

For example, JP-A-2011-145238 discloses a device that displays a plurality of binary scatter diagrams generated by combining two different elements in a matrix so that the analyst can select and analyze one of the scatter diagrams.

In this case, however, since a large number of scatter diagrams are displayed in a matrix, it may be difficult to determine the correlation between the elements depending on the arrangement of the scatter diagrams. Therefore, the analyst may have to repeatedly rearrange the binary scatter diagrams so that the correlation between the elements can be easily determined.

SUMMARY

Several aspects of the invention may provide a scatter diagram display device that can display a plurality of scatter diagrams so that the correlation between the elements can be easily determined. Several aspects of the invention may also provide a surface analyzer that includes the scatter diagram display device.

According to a first aspect of the invention, there is provided a scatter diagram display device including:
a principal component analysis section that performs principal component analysis on intensity or concentration map data that represents each element;
a priority level setting section that sets a priority level to each element based on the results of the principal component analysis performed by the principal component analysis section; and
a display control section that performs a control process that arranges a plurality of scatter diagrams generated by combining each element based on the priority level that has been set to each element by the priority level setting section, and displays the plurality of scatter diagrams on a display section.

According to a second aspect of the invention, there is provided a scatter diagram display device including:
a scatter diagram generation section that generates a plurality of scatter diagrams by combining each element based on intensity or concentration map data that represents each element;
a variance calculation section that calculates variance of each of the plurality of scatter diagrams generated by the scatter diagram generation section;
a priority level setting section that sets a priority level to each element based on the variance of each of the plurality of scatter diagrams calculated by the variance calculation section; and
a display control section that performs a control process that arranges the plurality of scatter diagrams generated by combining each element based on the priority level that has been set to each element by the priority level setting section, and displays the plurality of scatter diagrams on a display section.

According to a third aspect of the invention, there is provided a surface analyzer including one of the above scatter diagram display devices.

Figure 1:
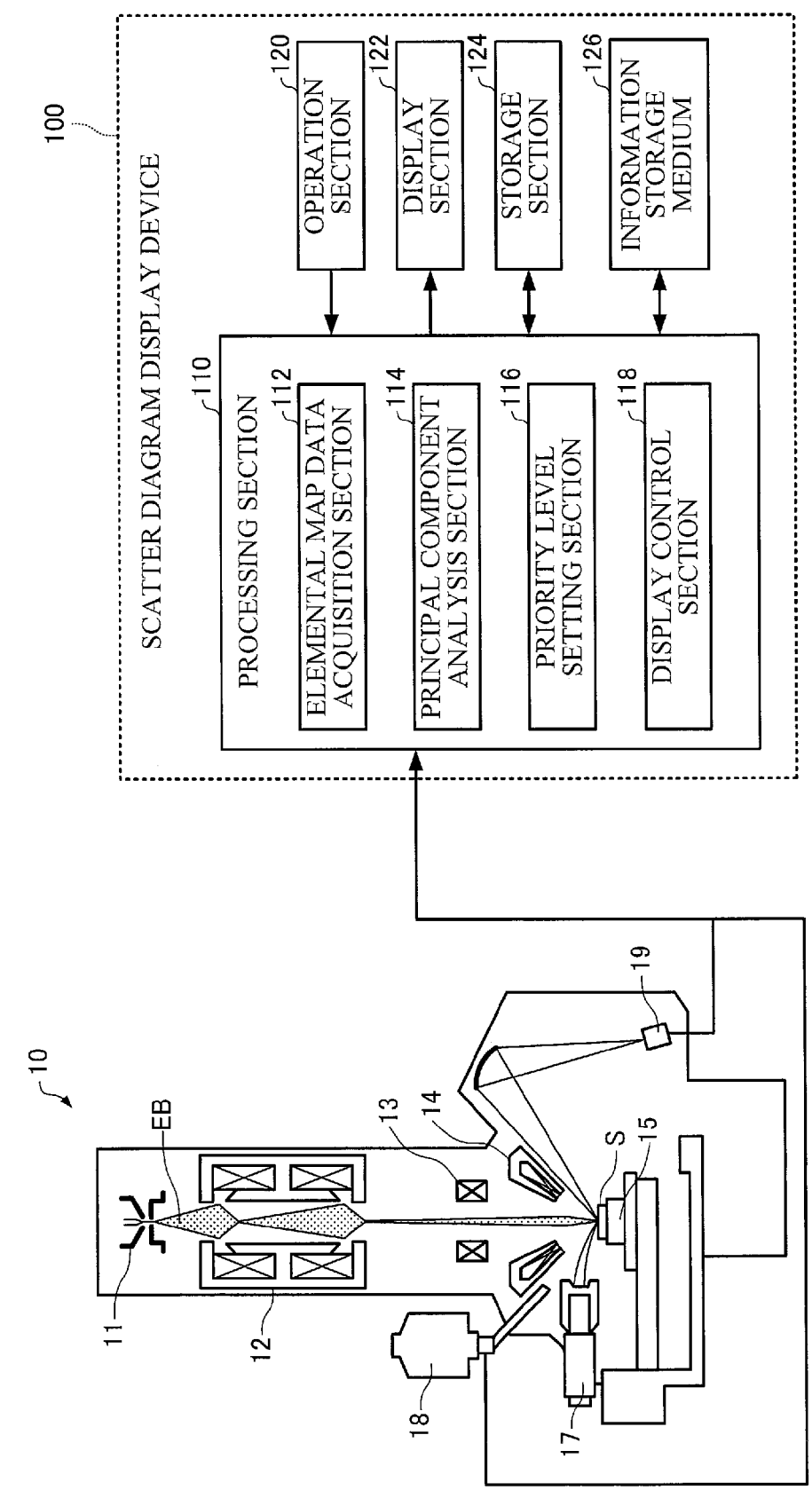
FIG. 1 schematically illustrates the configuration of a surface analyzer that includes a scatter diagram display device according to the first embodiment of the invention.

DETAILED DESCRIPTION OF THE EMBODIMENT (1) According to one embodiment of the invention, a scatter diagram display device includes:
a principal component analysis section that performs principal component analysis on intensity or concentration map data that represents each element;
a priority level setting section that sets a priority level to each element based on the results of the principal component analysis performed by the principal component analysis section; and
a display control section that performs a control process that arranges a plurality of scatter diagrams generated by combining each element based on the priority level that has been set to each element by the priority level setting section, and displays the plurality of scatter diagrams on a display section.

Since the scatter diagram display device sets the priority level to each element based on the results of the principal component analysis, and arranges the scatter diagrams based on the priority level, the scatter diagram display device can display a plurality of scatter diagrams so that the correlation between the elements can be easily determined. For example, the scatter diagram display device can automatically display a plurality of scatter diagrams so that the correlation between the elements can be easily determined.

(2) In the above scatter diagram display device, the priority level setting section may set the highest priority level to an element for which a principal component coefficient of a first principal component has the largest absolute value, and set the second highest priority level to an element for which a principal component coefficient of a second principal component has the largest absolute value.

The scatter diagram display device thus makes it possible to determine a combination of elements to which the greatest attention should be paid during phase analysis, and can display a plurality of scatter diagrams so that the correlation between the elements can be easily determined.

(3) In the above scatter diagram display device, the display control section may arrange the plurality of scatter diagrams in a matrix based on the priority level that has been set to each element by the priority level setting section to generate a scatter diagram matrix, and place a scatter diagram among the plurality of scatter diagrams generated by combining the element to which the highest priority level has been set with the element to which the second highest priority level has been set at the corner of the scatter diagram matrix.

The scatter diagram display device can thus display a plurality of scatter diagrams so that the correlation between the elements can be easily determined.

(4) In the above scatter diagram display device, the priority level setting section may set the highest priority level to an element for which a principal component coefficient of a first principal component has the largest absolute value, and set the second highest priority level to an element for which the principal component coefficient of the first principal component has the second largest absolute value.

The scatter diagram display device can thus display a plurality of scatter diagrams so that the correlation between the elements can be easily determined.

(5) According to another embodiment of the invention, a scatter diagram display device includes:
  a scatter diagram generation section that generates a plurality of scatter diagrams by combining each element based on intensity or concentration map data that represents each element;
  a variance calculation section that calculates variance of each of the plurality of scatter diagrams generated by the scatter diagram generation section;
  a priority level setting section that sets a priority level to each element based on the variance of each of the plurality of scatter diagrams calculated by the variance calculation section; and
  a display control section that performs a control process that arranges the plurality of scatter diagrams generated by combining each element based on the priority level that has been set to each element by the priority level setting section, and displays the plurality of scatter diagrams on a display section.

Since the scatter diagram display device sets the priority level to each element based on the variance of each scatter diagram, and arranges the scatter diagrams based on the priority level, the scatter diagram display device can display a plurality of scatter diagrams so that the correlation between the elements can be easily determined. For example, the scatter diagram display device can automatically display a plurality of scatter diagrams so that the correlation between the elements can be easily determined.

(6) In the above scatter diagram display device, the display control section may arrange the plurality of scatter diagrams in a matrix based on the priority level that has been set to each element by the priority level setting section to generate a scatter diagram matrix, and place a scatter diagram among the plurality of scatter diagrams generated by combining the element to which the highest priority level has been set with the element to which the second highest priority level has been set at the corner of the scatter diagram matrix.

The scatter diagram display device can thus display a plurality of scatter diagrams so that the correlation between the elements can be easily determined.

(7) According to another embodiment of the invention, a scatter diagram display method includes:
  a principal component analysis step that performs principal component analysis on intensity or concentration map data that represents each element;
  a priority level setting step that sets a priority level to each element based on the results of the principal component analysis performed by the principal component analysis step; and
  a display control step that performs a control process that arranges a plurality of scatter diagrams generated by combining each element based on the priority level that has been set to each element by the priority level setting step, and displays the plurality of scatter diagrams on a display section.

Since the scatter diagram display method sets the priority level to each element based on the results of the principal component analysis, and arranges the scatter diagrams based on the priority level, the scatter diagram display method can display a plurality of scatter diagrams so that the correlation between the elements can be easily determined.

(8) In the above scatter diagram display method, the priority level setting step may set the highest priority level to an element for which a principal component coefficient of a first principal component has the largest absolute value, and set the second highest priority level to an element for which a principal component coefficient of a second principal component has the largest absolute value.

The scatter diagram display method thus makes it possible to determine a combination of elements to which the greatest attention should be paid during phase analysis, and can display a plurality of scatter diagrams so that the correlation between the elements can be easily determined.

(9) In the above scatter diagram display method, the display control step may arrange the plurality of scatter diagrams in a matrix based on the priority level that has been set to each element by the priority level setting step to generate a scatter diagram matrix, and place a scatter diagram among the plurality of scatter diagrams generated by combining the element to which the highest priority level has been set with the element to which the second highest priority level has been set at the corner of the scatter diagram matrix.

The scatter diagram display method can thus display a plurality of scatter diagrams so that the correlation between the elements can be easily determined.

(10) In the above scatter diagram display method, the priority level setting step may set the highest priority level to an element for which a principal component coefficient of a first principal component has the largest absolute value, and set the second highest priority level to an element for which the principal component coefficient of the first principal component has the second largest absolute value.

The scatter diagram display method can thus display a plurality of scatter diagrams so that the correlation between the elements can be easily determined.

(11) According to another embodiment of the invention, a scatter diagram display method includes:

a scatter diagram generation step that generates a plurality of scatter diagrams by combining each element based on intensity or concentration map data that represents each element;

a variance calculation step that calculates variance of each of the plurality of scatter diagrams generated by the scatter diagram generation step;

a priority level setting step that sets a priority level to each element based on the variance of each of the plurality of scatter diagrams calculated by the variance calculation step; and a display control step that performs a control process that arranges the plurality of scatter diagrams generated by combining each element based on the priority level that has been set to each element by the priority level setting step, and displays the plurality of scatter diagrams on a display section.

Since the scatter diagram display method sets the priority level to each element based on the variance of each scatter diagram, and arranges the scatter diagrams based on the priority level, the scatter diagram display method can display a plurality of scatter diagrams so that the correlation between the elements can be easily determined.

(12) In the above scatter diagram display method, the display control step may arrange the plurality of scatter diagrams in a matrix based on the priority level that has been set to each element by the priority level setting step to generate a scatter diagram matrix, and place a scatter diagram among the plurality of scatter diagrams generated by combining the element to which the highest priority level has been set with the element to which the second highest priority level has been set at the corner of the scatter diagram matrix.

The scatter diagram display method can thus display a plurality of scatter diagrams so that the correlation between the elements can be easily determined.

(13) According to another embodiment of the invention, a surface analyzer includes the scatter diagram display device.

Since the surface analyzer includes the scatter diagram display device, the surface analyzer can display a plurality of scatter diagrams so that the correlation between the elements can be easily determined.

Exemplary embodiments of the invention are described in detail below with reference to the drawings. Note that the following exemplary embodiments do not unduly limit the scope of the invention as stated in the claims. Note also that all of the elements described below should not necessarily be taken as essential elements of the invention.

1. First Embodiment 1.1. Scatter Diagram Display Device

A scatter diagram display device according to a first embodiment of the invention is described below with reference to the drawings. FIG. 1 is a view schematically illustrating the configuration of a surface analyzer 1000 that includes a scatter diagram display device 100 according to the first embodiment. Note that the scatter diagram display device 100 need not necessarily be included in the surface analyzer 1000.

As illustrated in FIG. 1, the surface analyzer 1000 includes a surface analyzer main body 10 and the scatter diagram display device 100.

The surface analyzer 1000 applies electron beams EB to a specimen S, detects characteristic X-rays emitted (generated) from the specimen S upon application of the electron beams EB, and qualitatively or quantitatively analyzes the elements included in the specimen S. The surface analyzer 1000 can perform area analysis (map analysis) on the specimen S. The surface analyzer 1000 is an electron probe microanalyzer (EPMA), for example.

(1) Surface Analyzer Main Body

The surface analyzer main body 10 includes an electron gun 11, a condenser lens 12, a deflector 13, an objective lens 14, a specimen stage 15, a secondary electron detector 17, an energy-dispersive detector 18, and a wavelength-dispersive detector 19.

The electron gun 11 generates the electron beams EB. The electron gun 11 emits the electron beams EB that have been accelerated by applying a predetermined accelerating voltage toward the specimen S.

The condenser lens 12 is disposed in the subsequent stage of the electron gun 11 (on the downstream side of the electron gun 11 (that emits the electron beams EB)). The condenser lens 12 focuses the electron beams EB.

The deflector 13 is disposed in the subsequent stage of the condenser lens 12. The deflector 13 deflects the electron beams EB. A scan signal is input to the deflector 13 through a control circuit (not illustrated in FIG. 1), and the specimen S is scanned with the electron beams EB that have been focused by the condenser lens 12 and the objective lens 14.

The objective lens 14 is disposed in the subsequent stage of the deflector 13. The objective lens 14 focuses the electron beams EB on the specimen S to apply the electron beams EB to the specimen S as an electronic probe.

The specimen stage 15 supports the specimen S. The specimen S is placed on the specimen stage 15. The specimen stage 15 is moved by a stage-moving mechanism (not illustrated in FIG. 1) that includes a drive source (e.g., motor). The analysis position (analysis area (part)) on the specimen S to which the electron beams EB (electronic probe) are applied can be relatively moved by moving the specimen stage 15.

The secondary electron detector 17 detects secondary electrons released from the specimen S. The secondary electron detector 17 is an Everhart-Thornley detector (ET detector), for example. A secondary electron image (SEM image) can be obtained from the measurement results (output signal) of the secondary electron detector 17. The signal output from the secondary electron detector 17 is stored (recorded) in a storage section 124 included in the scatter diagram display device 100 as image data that is synchronized with the scan signal for the electron beams EB, for example.

The energy-dispersive detector 18 discriminates X-rays based on energy to obtain a spectrum. The energy-dispersive detector 18 detects the characteristic X-rays that are generated when the electron beams EB have been applied to the specimen S. The energy-dispersive detector 18 is an energy-dispersive X-ray spectrometer (EDS), for example.

The wavelength-dispersive detector 19 separates and detects the characteristic X-rays that are generated when the electron beams EB have been applied to the specimen S. The wavelength-dispersive detector 19 separates X-rays having a specific wavelength by utilizing Bragg reflection of X-rays due to an analyzing crystal, for example. The wavelength-dispersive detector 19 is a wavelength-dispersive X-ray spectrometer (WDS), for example.

The surface analyzer main body 10 can perform map analysis (area analysis) on the specimen S. Specifically, the surface analyzer main body 10 divides a predetermined range of the specimen S into pixels (unit areas), and measures the X-ray intensity at each pixel using the energy-dispersive detector 18 or the wavelength-dispersive detector 19 to obtain elemental map data (elemental distribution information). The elemental map data includes two-dimensional distribution information about an element. The elemental map data includes information about a two-dimensional position (coordinates) of an element and the X-ray intensity (or the concentration of an element) at each position. The elemental map data is obtained on an element basis. For example, the elemental map data that represents an element "a" includes the two-dimensional distribution information about the element "a". The elemental map data that represents the element a includes information about the position of the element "a" and the X-ray intensity of the element "a" (or the concentration of the element "a") at each position. The elemental map data output from the surface analyzer main body 10 is stored in the storage section 124 included in the scatter diagram display device 100, for example.

(2) Scatter Diagram Display Device

The scatter diagram display device 100 acquires the elemental map data obtained by the map analysis performed by the surface analyzer main body 10, performs principal component analysis on the acquired elemental map data, sets the priority level to each element based on the results of the principal component analysis, arranges the scatter diagrams based on the priority level, and displays the scatter diagrams on a display section 122. The scatter diagram display device 100 is implemented by a general-purpose computer such as a personal computer (PC), for example. The scatter diagram display device 100 includes a processing section 110, an operation section 120, the display section 122, the storage section 124, and an information storage medium 126.

The operation section 120 acquires an operation signal that corresponds to the operation performed by the user, and transmits the operation signal to the processing section 110. The operation section 120 is a button, a key, a touch panel display, or a microphone, for example.

The display section 122 displays an image generated by the processing section 110. The function of the display section 122 may be implemented by an LCD, a CRT, or the like. The display section 122 displays a plurality of scatter diagrams (scatter diagram matrix) generated by the processing section 110 (display control section 118), for example. The display section 122 also displays a secondary electron image, an elemental map, and the like.

The storage section 124 serves as a work area for the processing section 110. The function of the storage section 124 may be implemented by a RAM or the like. The storage section 124 stores a program, data, and the like that cause or allow the processing section 110 to perform various calculation processes and control processes. The storage section 124 is also used to temporarily store the results of calculations performed by the processing section 110 according to a program, for example.

The information storage medium 126 (computer-readable medium) stores a program, data, and the like. The function of the information storage medium 126 may be implemented by an optical disk (CD or DVD), a magneto-optical disk (MO), a magnetic disk, a hard disk, a magnetic tape, a memory (ROM), or the like. The processing section 110 performs various processes according to the first embodiment based on the program (data) stored in the information storage medium 126. The information storage medium 126 may store a program that causes a computer to function as each section of the processing section 110.

The processing section 110 performs various calculation processes according to the program stored in the storage section 124. The processing section 110 functions as an elemental map data acquisition section 112, a principal component analysis section 114, a priority level setting section 116, and the display control section 118 (described below) by executing the program stored in the storage section 124. The function of the processing section 110 may be implemented by hardware such as a processor (e.g., CPU or DSP) or ASIC (e.g., gate array), or a program. Note that at least part of the processing section 110 may be implemented by hardware (dedicated circuit). The processing section 110 includes the elemental map data acquisition section 112, the principal component analysis section 114, the priority level setting section 116, and the display control section 118.

The elemental map data acquisition section 112 acquires a plurality of pieces of elemental map data. For example, the elemental map data acquisition section 112 acquires information about each piece of elemental map data obtained by the area analysis performed by the surface analyzer main body 10. Note that the elemental map data acquisition section 112 may acquire information about a plurality of pieces of elemental map data selected by the user from the elemental map data obtained by the area analysis performed by the surface analyzer main body 10. The elemental map data obtained by the area analysis performed by the surface analyzer main body 10 is stored in the storage section 124, and the elemental map data acquisition section 112 reads the elemental map data from the storage section 124.

The principal component analysis section 114 performs the principal component analysis on the plurality of pieces of elemental map data acquired by the elemental map data acquisition section 112.

The term "principal component analysis" used herein refers to a multivariate analysis (statistics) method that calculates a small number of characteristic variables (composite variables) from multivariate data, the characteristic variables representing the characteristics of the data set. The composite variable (principal component) u is represented by the following expression (1).

$$u_i = a_1 x_{1,i} + a_2 x_{2,i} + \ldots + a_{N-1} x_{N-1,i} + a_N x_{N,i} \quad (1)$$

where, N is the number of variables, i is a natural number, x is data of each variable, and $a_1, a_2 \ldots a_{N-1}$, and $a_N$ are composite variable coefficients (principal component coefficients).

The composite variable coefficients (principal component coefficients) $a_1, a_2 \ldots a_{N-1}$, and $a_N$ are calculated so that the variance of the composite variable u becomes a maximum.

Note that the composite variable coefficients (principal component coefficients) satisfy the following relationship.

$$a_1^2+a_2^2+\ldots+a_{N-1}^2+a_N^2=1$$

When calculating the composite variable coefficients (principal component coefficients) $a_1, a_2 \ldots a_{N-1}$, and $a_N$, the variance-covariance matrix of the original data set is calculated, and the eigenvalue problem of the variance-covariance matrix is solved. The eigenvector that is the solution to the eigenvalue problem corresponds to the coefficients $a_1$, $a_2 \ldots a_{N-1}$, and $a_N$. The resulting N (i.e., the same number as the number of pieces of data included in the original data set) principal components include a first principal component, a second principal component . . . and an Nth principal component (in descending order of the eigenvalue).

The principal component analysis section 114 performs the principal component analysis on the data (intensity value or concentration value) that represents each pixel of the plurality of pieces of elemental map data acquired by the elemental map data acquisition section 112 to calculate the principal component coefficient of the first principal component and the principal component coefficient of the second principal component.

The priority level setting section 116 sets the priority level to each element based on the results of the principal component analysis performed by the principal component analysis section 114. The priority level setting section 116 sets the highest priority level to an element for which the principal component coefficient of the first principal component has the largest absolute value, and sets the second highest priority level to an element for which the principal component coefficient of the second principal component has the largest absolute value.

The priority level setting section 116 sets the third highest priority level to an element (other than the element to which the second highest priority level has been set) for which the principal component coefficient of the first principal component has the second largest absolute value, and sets the fourth highest priority level to an element (other than the element to which the second highest priority level has been set) for which the absolute value of the principal component coefficient of the first principal component is the third largest, for example. The priority level setting section 116 similarly sets the priority level to the remaining elements in descending order of the principal component coefficient of the first principal component.

The display control section 118 performs a control process that arranges the plurality of scatter diagrams generated by combining each element based on the priority level that has been set to each element by the priority level setting section 116, and displays the plurality of scatter diagrams on the display section 122. For example, the display control section 118 arranges the plurality of scatter diagrams (generated by combining each element) in a matrix based on the priority level to generate a scatter diagram matrix.

Figure 2:
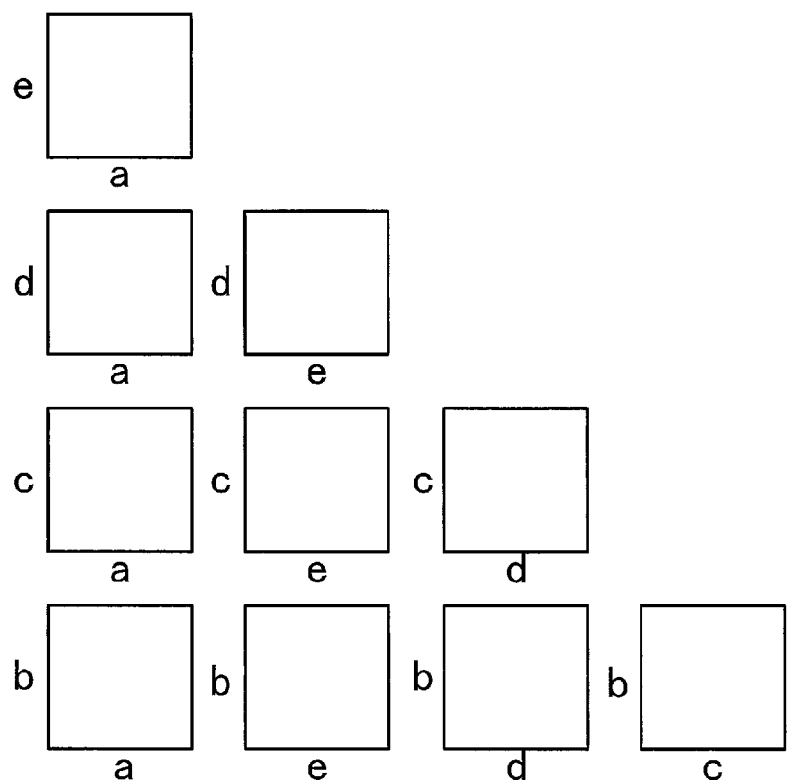
FIG. 2 schematically illustrates an example of a scatter diagram matrix.

FIG. 2 is a view schematically illustrating an example of the scatter diagram matrix. In FIG. 2, each scatter diagram is illustrated in a simplified manner.

As illustrated in FIG. 2, the scatter diagram matrix has a configuration in which scatter diagrams (binary scatter diagrams) generated by combining two different elements are arranged in a matrix. In the example illustrated in FIG. 2, scatter diagrams generated by combining two elements among elements "a", "b", "c", "d", and "e" are arranged in the scatter diagram matrix. In the example illustrated in FIG. 2, the scatter diagrams that are arranged side by side in the vertical direction are identical as to the element indicated by the horizontal axis, and the scatter diagrams that are arranged side by side in the horizontal direction are identical as to the element indicated by the vertical axis.

The display control section 118 places the scatter diagram ((a, b) scatter diagram) generated by combining the element (e.g., element "a") to which the highest priority level has been set with the element (e.g., element "b") to which the second highest priority level has been set at the corner (lower left corner) of the scatter diagram matrix. The display control section 118 arranges the scatter diagrams ((a, c) scatter diagram, (a, d) scatter diagram, and (a, e) scatter diagram) generated by combining the element to which the highest priority level has been set with the element (e.g., element c, d, or e) to which the third, fourth, or fifth highest priority level has been set in the vertical direction from the corner of the scatter diagram matrix in descending order of the priority level.

The display control section 118 then arranges the scatter diagrams ((b, c) scatter diagram, (b, d) scatter diagram, and (b, e) scatter diagram) generated by combining the element to which the second highest priority level has been set with the element (e.g., element c, d, or e) to which the third, fourth, or fifth highest priority level has been set in the horizontal direction toward the corner of the scatter diagram matrix in descending order of the priority level. The remaining scatter diagrams ((c, d) scatter diagram, (c, e) scatter diagram, and (d, e) scatter diagram) are arranged in the same manner as described above to generate the scatter diagram matrix.

The display control section 118 displays the generated scatter diagram matrix on the display section 122.

Figure 3:
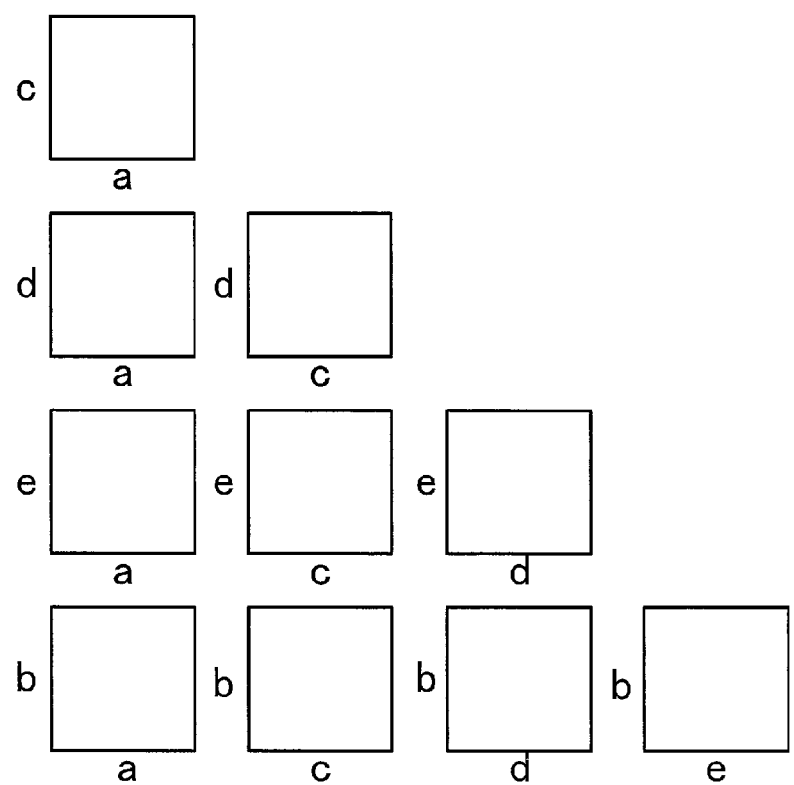
FIG. 3 schematically illustrates a modification of the scatter diagram matrix.

Note that the arrangement of the scatter diagrams in the scatter diagram matrix generated by the display control section 118 is not limited to the example illustrated in FIG. 2. FIG. 3 is a view schematically illustrating a modification of the scatter diagram matrix. In FIG. 3, each scatter diagram is illustrated in a simplified manner. As illustrated in FIG. 3, the display control section 118 arranges the scatter diagrams ((a, c) scatter diagram, (a, d) scatter diagram, and (a, e) scatter diagram) generated by combining the element to which the highest priority level has been set with the element (e.g., element "c", "d", or "e") to which the third, fourth, or fifth highest priority level has been set in the vertical direction toward the corner of the scatter diagram matrix in descending order of the priority level. The display control section 118 then arranges the scatter diagrams ((b, c) scatter diagram, (b, d) scatter diagram, and (b, e) scatter diagram) generated by combining the element to which the second highest priority level has been set with the element (e.g., element "c", "d", or "e") to which the third, fourth, or fifth highest priority level has been set in the horizontal direction from the corner of the scatter diagram matrix in descending order of the priority level. The remaining scatter diagrams ((c, d) scatter diagram, (c, e) scatter diagram, and (d, e) scatter diagram) are arranged in the same manner as described above to generate the scatter diagram matrix.

1.2. Scatter Diagram Display Method

Figures 4, 5:
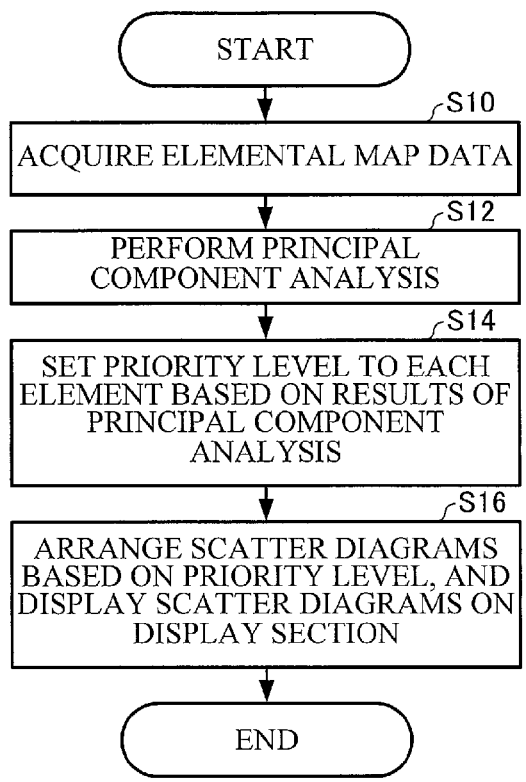
FIG. 4 is a flowchart illustrating an example of a scatter diagram display method that is implemented by a scatter diagram display device according to the first embodiment.
FIG. 5 is a table illustrating the results of principal component analysis performed by a principal component analysis section.

A scatter diagram display method that is implemented by the scatter diagram display device 100 according to the first embodiment is described below with reference to the drawings. FIG. 4 is a flowchart illustrating an example of the scatter diagram display method that is implemented by the scatter diagram display device 100 according to the first embodiment.

The elemental map data acquisition section 112 acquires a plurality of pieces of elemental map data (step S10).

For example, the elemental map data acquisition section 112 acquires Al elemental map data, Mg elemental map data, Si elemental map data, Fe elemental map data, and Zn elemental map data in the step S10.

The principal component analysis section 114 performs the principal component analysis on the Al elemental map data, the Mg elemental map data, the Si elemental map data, the Fe elemental map data, and the Zn elemental map data acquired by the elemental map data acquisition section 112 (step S12).

More specifically, the principal component analysis section 114 performs the principal component analysis on the data (i.e., the X-ray intensity value or the concentration value of each element) that represents each pixel of the Al elemental map data, the Mg elemental map data, the Si elemental map data, the Fe elemental map data, and the Zn elemental map data. The principal component analysis section 114 synthesizes five elements (i.e., the intensity values (or the concentration values) of the five elements (Al, Mg, Si, Fe, and Zn)) to generate a new component. Specifically, N in the expression (1) is 5. The principal component analysis section 114 performs the principal component analysis on the Al elemental map data, the Mg elemental map data, the Si elemental map data, the Fe elemental map data, and the Zn elemental map data to calculate the principal component coefficients of the first to fifth principal components.

FIG. 5 is a view (table) illustrating the results of the principal component analysis performed by the principal component analysis section 114. The principal component analysis section 114 calculates the principal component coefficient of the first principal component and the principal component coefficient of the second principal component (see FIG. 5) by performing the principal component analysis.

The priority level setting section 116 sets the priority level to each element based on the results of the principal component analysis performed by the principal component analysis section 114 (step S14).

More specifically, the priority level setting section 116 sets the highest priority level to Al for which the principal component coefficient of the first principal component has the largest absolute value, and sets the second highest priority level to Fe for which the principal component coefficient of the second principal component has the largest absolute value. The priority level setting section 116 sets the third highest priority level to Zn for which the principal component coefficient of the first principal component has the second largest absolute value, sets the fourth highest priority level to Si for which the absolute value of the principal component coefficient of the first principal component is the third largest, and sets the fifth highest priority level to Mg for which the absolute value of the principal component coefficient of the first principal component is the fourth largest (excluding Fe to which the second highest priority level has been set). Specifically, the priority level setting section 116 sets a higher priority level in order of Al, Fe, Zn, Si, and Mg.

The display control section 118 performs the control process that arranges a plurality of scatter diagrams generated by combining each element based on the priority level that has been set to each element by the priority level setting section 116, and displays the plurality of scatter diagrams on the display section 122 (step S16).

More specifically, the display control section 118 generates a scatter diagram ((Al, Fe) scatter diagram) by combining Al (to which the highest priority level has been set) with Fe (to which the second highest priority level has been set), and places the generated scatter diagram at the lower left corner of the scatter diagram matrix.

The display control section 118 arranges the scatter diagrams ((Al, Zn) scatter diagram, (Al, Si) scatter diagram, and (Al, Mg) scatter diagram) generated by combining Al (to which the highest priority level has been set) with Zn, Si, or Mg (to which the third, fourth, or fifth highest priority level has been set) in the vertical direction from the corner of the scatter diagram matrix in descending order of the priority level. The display control section 118 then arranges the scatter diagrams ((Fe, Zn) scatter diagram, (Fe, Si) scatter diagram, and (Fe, Mg) scatter diagram) generated by combining Fe (to which the second highest priority level has been set) with Zn, Si, or Mg (to which the third, fourth, or fifth highest priority level has been set) in the horizontal direction toward the corner of the scatter diagram matrix in descending order of the priority level. The display control section 118 then arranges the remaining scatter diagrams ((Zn, Si) scatter diagram, (Zn, Mg) scatter diagram, and (Si, Mg) scatter diagram) in the same manner as described above to generate the scatter diagram matrix.

Figures 6, 7:
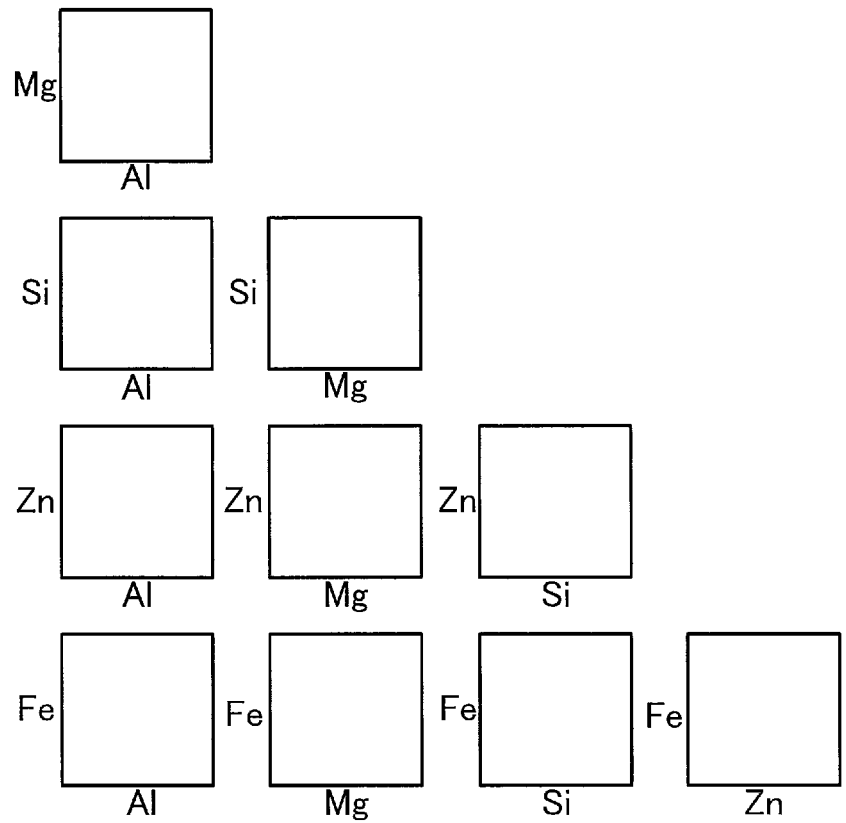
FIG. 6 schematically illustrates a scatter diagram matrix generated by a display control section.
FIG. 7 is a table illustrating examples of a principal component coefficient of a first principal component.

FIG. 6 is a view schematically illustrating the scatter diagram matrix generated by the display control section 118.

The display control section 118 performs the control process that displays the scatter diagram matrix illustrated in FIG. 6 on the display section 122. The processing section 110 then terminates the process.

The scatter diagram display device 100 has the following features, for example.

The scatter diagram display device 100 includes the principal component analysis section 114 that performs the principal component analysis on intensity or concentration map data that represents each element, the priority level setting section 116 that sets the priority level to each element based on the results of the principal component analysis performed by the principal component analysis section 114, and the display control section 118 that performs the control process that arranges a plurality of scatter diagrams generated by combining each element based on the priority level that has been set to each element by the priority level setting section 116, and displays the plurality of scatter diagrams on the display section 122. Since the scatter diagram display device 100 sets the priority level to each element based on the results of the principal component analysis, and arranges the scatter diagrams based on the priority level, it is possible to determine (find) the scatter diagram generated by combining characteristic elements that reflect the correlation between the elements included in the specimen S (i.e., the scatter diagram to which the greatest attention should be paid during phase analysis), and place the scatter diagram at a position (i.e., the corner of the scatter diagram matrix) at which the correlation between the elements can be easily determined. Therefore, the scatter diagram display device 100 can display a plurality of scatter diagrams (scatter diagram matrix) so that the correlation between the elements can be easily determined. For example, the scatter diagram display device 100 can automatically display a plurality of scatter diagrams (scatter diagram matrix) so that the correlation between the elements can be easily determined.

The priority level setting section 116 included in the scatter diagram display device 100 sets the highest priority level to an element for which the principal component coefficient of the first principal component has the largest absolute value, and sets the second highest priority level to an element for which the principal component coefficient of the second principal component has the largest absolute value. This makes it possible to determine (find) the scatter diagram to which the greatest attention should be paid during phase analysis. The reasons therefor are described below.

An example in which the priority level is determined by comparing only the principal component coefficients of the first principal component is described below. FIG. 7 is a view (table) illustrating an example of the principal component coefficient of the first principal component.

In the example illustrated in FIG. 7, the absolute values of the principal component coefficients for Al (principal component coefficient=2.1) and Mg (principal component coefficient=2.1) are large and identical. If the priority level is determined by comparing only the principal component coefficients of the first principal component, the highest priority level is set to Al, and the second highest priority level is set to Mg. Note that the highest priority level may be set to Mg, and the second highest priority level may be set to Al. In either case, a scatter diagram is generated by combining Al with Mg when a scatter diagram is generated by combining the element to which the highest priority level has been set with the element to which the second highest priority level has been set.

Figure 8:
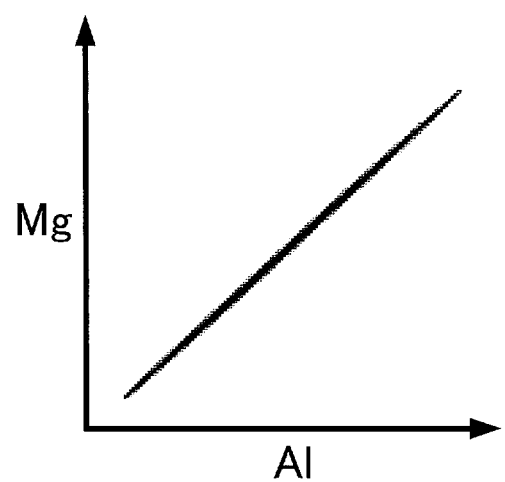
FIG. 8 is a scatter diagram generated by combining Al with Mg.

As illustrated in FIG. 8, the scatter diagram generated by combining Al with Mg has a structure in which data is plotted linearly. A combination of two elements that generate the scatter diagram illustrated in FIG. 8 (in which data is plotted linearly) is not a combination of characteristic elements that reflect the correlation between the elements during phase analysis, and a scatter diagram in which data is plotted linearly is not a scatter diagram to which the greatest attention should be paid.

Since the scatter diagram display device 100 sets the highest priority level to an element for which the principal component coefficient of the first principal component has the largest absolute value, and sets the second highest priority level to an element for which the principal component coefficient of the second principal component has the largest absolute value, it is possible to avoid a situation in which a combination of elements that generate the scatter diagram illustrated in FIG. 8 (in which data is plotted linearly) are selected. A combination of the first principal component and the second principal component used for the principal component analysis is a combination for which the variance becomes a maximum. Therefore, a scatter diagram generated by combining an element for which the principal component coefficient of the first principal component has the largest absolute value with an element for which the principal component coefficient of the second principal component has the largest absolute value is considered to be a scatter diagram generated by combining characteristic elements that provide large variance (i.e., a scatter diagram to which the greatest attention should be paid during phase analysis).

The scatter diagram display device 100 makes it possible to determine (find) the scatter diagram to which the greatest attention should be paid during phase analysis by setting the highest priority level to an element for which the principal component coefficient of the first principal component has the largest absolute value, and setting the second highest priority level to an element for which the principal component coefficient of the second principal component has the largest absolute value.

Figure 13:
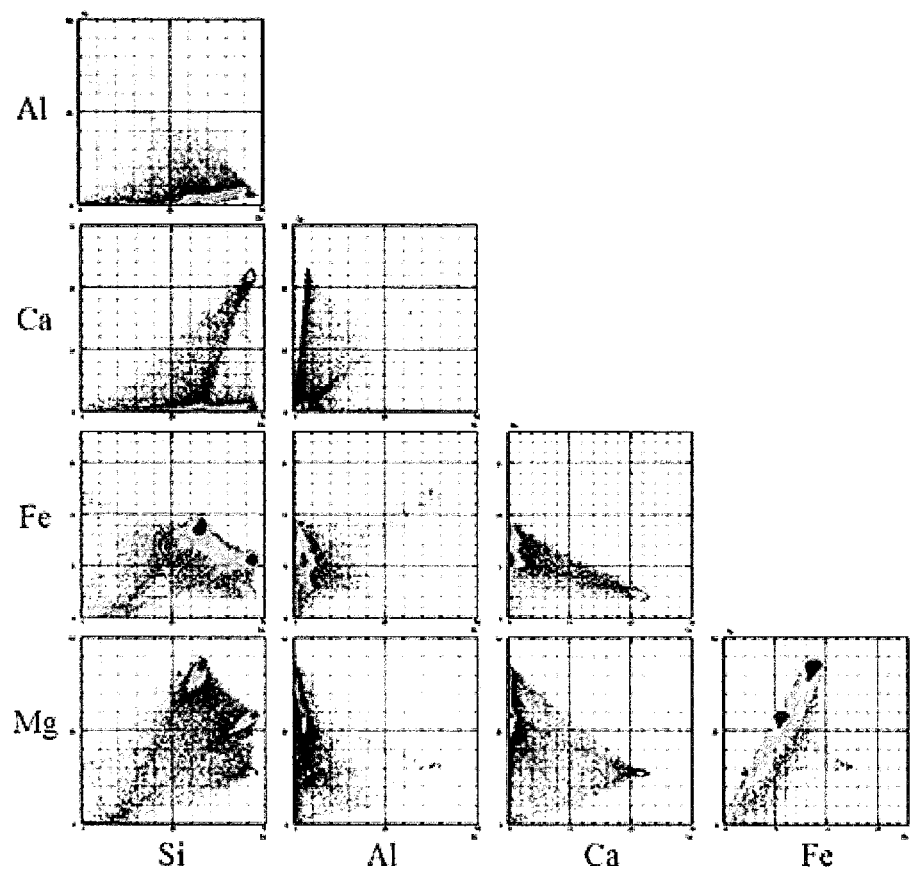
FIG. 13 illustrates an example of a scatter diagram matrix.

The display control section 118 included in the scatter diagram display device 100 arranges a plurality of scatter diagrams in a matrix based on the priority level that has been set to each element by the priority level setting section 116 to generate the scatter diagram matrix, and places the scatter diagram generated by combining the element to which the highest priority level has been set with the element to which the second highest priority level has been set at the corner of the scatter diagram matrix. When the user observes the scatter diagram matrix that is displayed on the display, it is considered that the user initially sees the origin (corner) of the scatter diagram matrix to check the scatter diagram situated at the corner of the scatter diagram matrix, and then moves the line of sight in the horizontal direction or the vertical direction. Therefore, when the scatter diagram to which the greatest attention should be paid is placed at the corner of the scatter diagram matrix, the user can determine the most important combination of elements at the first glance. When the name of each element included in the scatter diagram matrix is displayed as illustrated in FIG. 13, the name of the element that corresponds to the vertical axis and the name of the element that corresponds to the horizontal axis are displayed in the vicinity of only the scatter diagram that is situated at the corner of the scatter diagram matrix. Therefore, the user can immediately determine the two elements represented by the scatter diagram which is situated at the corner of the scatter diagram matrix and to which the greatest attention should be paid.

The scatter diagram display method that is implemented by the scatter diagram display device 100 includes a principal component analysis step that performs the principal component analysis on the intensity or concentration map data that represents each element (step S12), a priority level setting step that sets the priority level to each element based on the results of the principal component analysis performed by the principal component analysis step (step S14), and a display control step that performs the control process that arranges a plurality of scatter diagrams generated by combining each element based on the priority level that has been set to each element by the priority level setting step, and displays the plurality of scatter diagrams on the display section 122 (step S16). Since the scatter diagram display method sets the priority level to each element based on the results of the principal component analysis, and arranges the scatter diagrams based on the priority level, it is possible to determine (find) the scatter diagram generated by combining characteristic elements that reflect the correlation between the elements included in the specimen S (i.e., the scatter diagram to which the greatest attention should be paid during phase analysis), and place the scatter diagram at a position (i.e., the corner of the scatter diagram matrix) at which the correlation between the elements can be easily determined. Therefore, the scatter diagram display method can display a plurality of scatter diagrams (scatter diagram matrix) so that the correlation between the elements can be easily determined.

Since the surface analyzer 1000 includes the scatter diagram display device 100, the surface analyzer 1000 can display a plurality of scatter diagrams (scatter diagram matrix) so that the correlation between the elements can be easily determined.

2. Second Embodiment 2.1. Scatter Diagram Display Device

Figure 9:
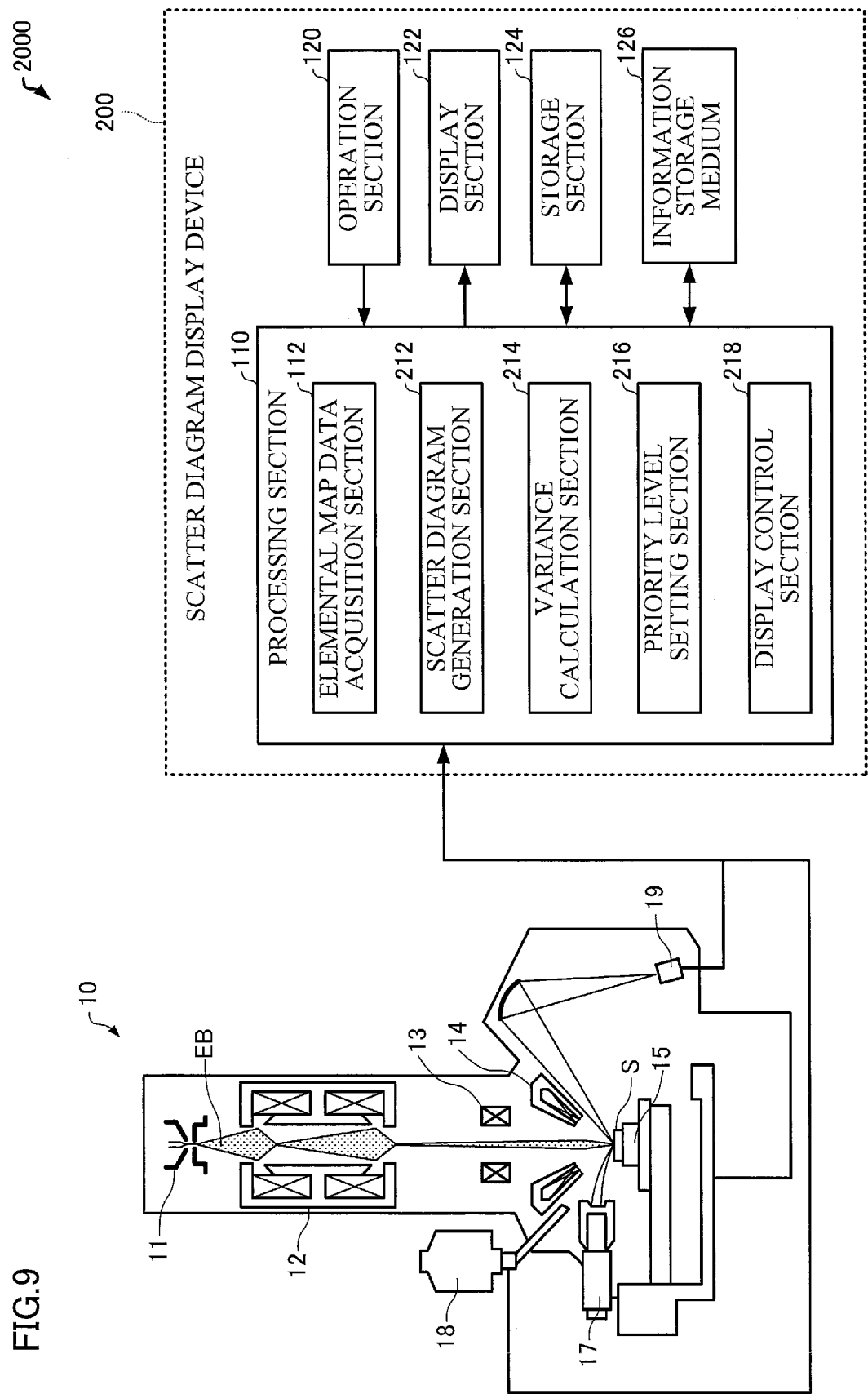
FIG. 9 schematically illustrates the configuration of a surface analyzer that includes a scatter diagram display device according to the second embodiment of the invention.

A scatter diagram display device according to a second embodiment of the invention is described below with reference to the drawings. FIG. 9 is a view schematically illustrating the configuration of a surface analyzer 2000 that includes a scatter diagram display device 200 according to the second embodiment. Note that the scatter diagram display device 200 need not necessarily be included in the surface analyzer 2000.

The elements included in the scatter diagram display device 200 and the surface analysis device 2000 according to the second embodiment that are identical in function to those included in the scatter diagram display device 100 and the surface analyzer 1000 according to the first embodiment are indicated by the same reference signs (symbols), and description thereof is omitted.

The scatter diagram display device 100 according to the first embodiment sets the priority level to each element based on the results of the principal component analysis, and arranges the scatter diagrams based on the priority level.

The scatter diagram display device 200 according to the second embodiment sets the priority level to each element based on the variance of each scatter diagram, and arranges the scatter diagrams based on the priority level.

The processing section 110 included in the scatter diagram display device 200 functions as an elemental map data acquisition section 112, a scatter diagram generation section 212, a variance calculation section 214, a priority level setting section 216, and a display control section 218 (described below) by executing the program stored in the storage section 124. The processing section 110 includes the elemental map data acquisition section 112, the scatter diagram generation section 212, the variance calculation section 214, the priority level setting section 216, and the display control section 218.

The elemental map data acquisition section 112 acquires a plurality of pieces of elemental map data.

The scatter diagram generation section 212 combines each element based on the elemental map data to generate a plurality of scatter diagrams. The scatter diagram generation section 212 generates the scatter diagrams (binary scatter diagrams) using every possible combination of two different elements among the elements represented by the elemental map data acquired by the elemental map data acquisition section 112. For example, when n (n is a natural number equal to or larger than 3) pieces of elemental map data have been acquired by the elemental map data acquisition section 112, the scatter diagram generation section 212 generates (n×(n−1)/2) scatter diagrams.

The variance calculation section 214 calculates the variance of each scatter diagram generated by the scatter diagram generation section 212. The scatter diagram is generated by plotting bivariate data in a plane. For example, the variance calculation section 214 uses the following expression (that calculates two-dimensional variance) when calculating the variance of the scatter diagram.

$$Cov(X,Y)=E[(X-E[X])(Y-E[Y])]$$

(Cov(X, Y): covariance of two random variables X and Y, E: expected value)

The priority level setting section 216 sets the priority level to each element based on the variance of each scatter diagram calculated by the variance calculation section 214. Specifically, the priority level setting section 216 selects the scatter diagram that has the largest variance from the scatter diagrams for which the variance has been calculated by the variance calculation section 214, sets the highest priority level to one of the two elements represented by the selected scatter diagram, and sets the second highest priority level to the other of the two elements represented by the selected scatter diagram. Note that the highest priority level may be arbitrarily set to either of the two elements represented by the scatter diagram that has the largest variance when generating the scatter diagram matrix. For example, a rule (e.g., the highest priority level is set to an element having a smaller atomic number) may be set in advance.

The priority level setting section 216 then selects the scatter diagram that has the largest variance from the scatter diagrams generated by combining the element to which the highest priority level has been set with an element among the elements other than the element to which the highest priority level has been set and the element to which the second highest priority level has been set. The priority level setting section 216 sets the third highest priority level to the element represented by the selected scatter diagram that is other than the element to which the highest priority level has been set.

Likewise, the priority level setting section 216 then selects the scatter diagram that has the second largest variance from the scatter diagrams generated by combining the element to which the highest priority level has been set with an element among the elements other than the element to which the highest priority level has been set and the element to which the second highest priority level has been set, and sets the fourth highest priority level to the element represented by the selected scatter diagram that is other than the element to which the highest priority level has been set. The priority level setting section 216 sets the priority level to the remaining elements in the same manner as described above.

Although an example has been described above in which the priority level setting section 216 sequentially selects the scatter diagram that has a larger variance from the scatter diagrams generated by combining the element to which the highest priority level has been set with an element among the elements other than the element to which the highest priority level has been set and the element to which the second highest priority level has been set, and sets the priority level to the element represented by the selected scatter diagram, the priority level setting section 216 may sequentially select the scatter diagram that has a larger variance from the scatter diagrams generated by combining the element to which the second highest priority level has been set with an element among the elements other than the element to which the highest priority level has been set and the element to which the second highest priority level has been set, and set the priority level to the element represented by the selected scatter diagram.

The display control section 218 performs a control process that arranges a plurality of scatter diagrams generated by combining each element based on the priority level that has been set to each element by the priority level setting section 216, and displays the plurality of scatter diagrams on the display section 122. For example, the display control section 218 arranges the plurality of scatter diagrams (generated by combining each element) in a matrix based on the priority level to generate a scatter diagram matrix. The display control section 218 displays the generated scatter diagram matrix on the display section 122. The process performed by the display control section 218 is the same as the process performed by the display control section 118 included in the scatter diagram display device 100 according to the first embodiment, and description thereof is omitted.

2.2. Scatter Diagram Display Method

Figure 10:
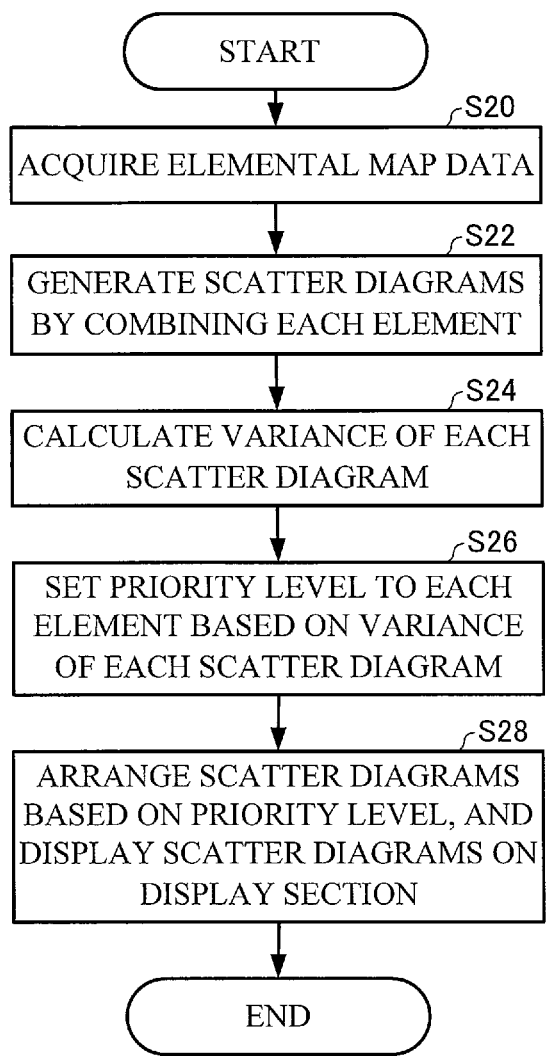
FIG. 10 is a flowchart illustrating an example of a scatter diagram display method that is implemented by a scatter diagram display device according to the second embodiment.

A scatter diagram display method that is implemented by the scatter diagram display device 200 according to the second embodiment is described below with reference to the drawings. FIG. 10 is a flowchart illustrating an example of the scatter diagram display method that is implemented by the scatter diagram display device 200 according to the second embodiment.

The elemental map data acquisition section 112 acquires a plurality of pieces of elemental map data (step S20).

For example, the elemental map data acquisition section 112 acquires Al elemental map data, Mg elemental map data, Si elemental map data, Fe elemental map data, and Zn elemental map data in the step S20.

The scatter diagram generation section 212 generates a plurality of scatter diagrams by combining each element (Al, Mg, Si, Fe, Zn) based on the Al elemental map data, the Mg elemental map data, the Si elemental map data, the Fe elemental map data, and the Zn elemental map data acquired by the elemental map data acquisition section 112 (step S22).

Specifically, the scatter diagram generation section 212 generates an (Al, Mg) scatter diagram, an (Al, Si) scatter diagram, an (Al, Fe) scatter diagram, an (Al, Zn) scatter diagram, an (Mg, Si) scatter diagram, an (Mg, Fe) scatter diagram, an (Mg, Zn) scatter diagram, an (Si, Fe) scatter diagram, an (Si, Zn) scatter diagram, and an (Fe, Zn) scatter diagram.

The variance calculation section 214 calculates the variance of each scatter diagram generated by the scatter diagram generation section 212 (step S24).

Figures 11, 12:
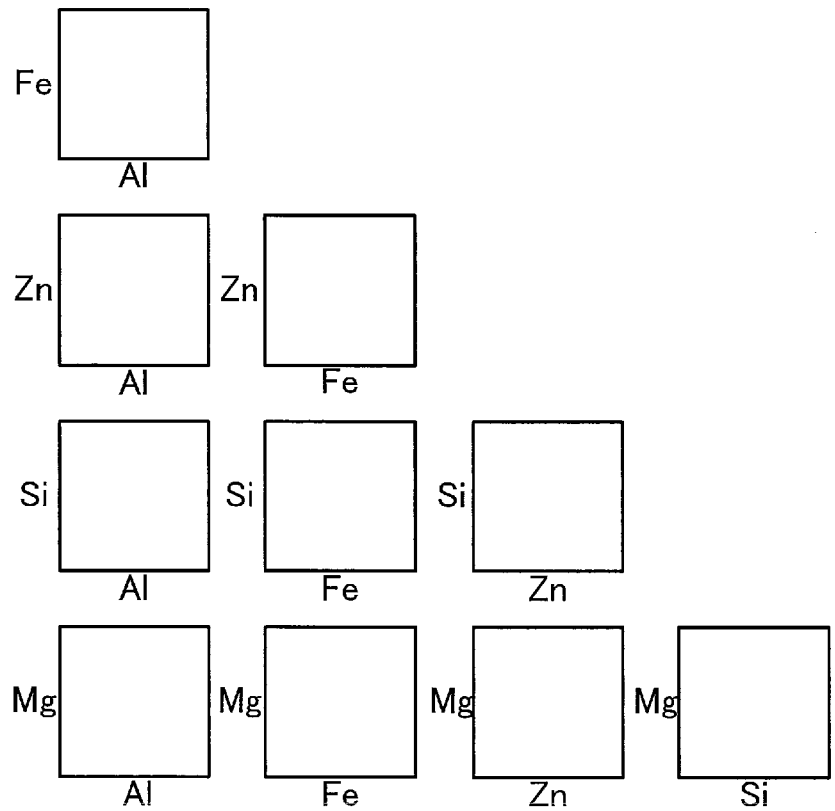
FIG. 11 is a table illustrating the variance of each scatter diagram calculated by a variance calculation section.
FIG. 12 schematically illustrates a scatter diagram matrix generated by a display control section.

FIG. 11 is a view (table) illustrating the variance of each scatter diagram calculated by the variance calculation section 214.

The priority level setting section 216 sets the priority level to each element based on the variance of each scatter diagram calculated by the variance calculation section 214 (step S26).

When the variance of each scatter diagram has been calculated as illustrated in FIG. 11, the priority level setting section 216 selects the (Al, Mg) scatter diagram (variance=24) that has the largest variance, sets the highest priority level to Al represented by the (Al, Mg) scatter diagram, and sets the second highest priority level to Mg represented by the (Al, Mg) scatter diagram.

The priority level setting section 216 then selects the (Al, Si) scatter diagram that has the largest variance from the scatter diagrams ((Al, Si) scatter diagram (variance=18), (Al, Fe) scatter diagram (variance=3), and (Al, Zn) scatter diagram (variance=9)) generated by combining Al with an element among the elements other than Al and Mg, and sets the third highest priority level to Si.

The priority level setting section 216 then selects the (Al, Zn) scatter diagram that has the second largest variance from the scatter diagrams generated by combining Al with an element among the elements other than Al and Mg, and sets the fourth highest priority level to Zn. The priority level setting section 216 then selects the (Al, Fe) scatter diagram that has the third largest variance, and sets the fifth highest priority level to Fe.

The priority level setting section 216 thus sets a higher priority level in order of Al, Mg, Si, Zn, and Fe.

The display control section 218 performs the control process that arranges a plurality of scatter diagrams generated by combining each element based on the priority level that has been set to each element by the priority level setting section 216, and displays the plurality of scatter diagrams on the display section 122 (step S28).

More specifically, the display control section 218 places the scatter diagram ((Al, Mg) scatter diagram) generated by combining Al (to which the highest priority level has been set) with Mg (to which the second highest priority level has been set) at the lower left corner of the scatter diagram matrix.

The display control section 218 arranges the scatter diagrams ((Al, Si) scatter diagram, (Al, Zn) scatter diagram, and (Al, Fe) scatter diagram) generated by combining Al (to which the highest priority level has been set) with Si, Zn, or Fe (to which the third, fourth, or fifth highest priority level has been set) in the vertical direction from the corner of the scatter diagram matrix in descending order of the priority level. The display control section 218 then arranges the scatter diagrams ((Mg, Si) scatter diagram, (Mg, Zn) scatter diagram, and (Mg, Fe) scatter diagram) generated by combining Mg (to which the second highest priority level has been set) with Si, Zn, or Fe (to which the third, fourth, or fifth highest priority level has been set) in the horizontal direction toward the corner of the scatter diagram matrix in descending order of the priority level. The display control section 218 then arranges the remaining scatter diagrams ((Si, Zn) scatter diagram, (Si, Fe) scatter diagram, and (Zn, Fe) scatter diagram) in the same manner as described above to generate the scatter diagram matrix.

FIG. 12 is a view schematically illustrating the scatter diagram matrix generated by the display control section 218. In FIG. 12, each scatter diagram is illustrated in a simplified manner.

The display control section 218 displays the generated scatter diagram matrix on the display section 122. The processing section 110 then terminates the process.

The scatter diagram display device 200 has the following features, for example.

The scatter diagram display device 200 includes the scatter diagram generation section 212 that generates a plurality of scatter diagrams by combining each element based on the intensity or concentration map data that represents each element, the variance calculation section 214 that calculates the variance of each scatter diagram generated by the scatter diagram generation section 212, the priority level setting section 216 that sets the priority level to each element based on the variance of each scatter diagram calculated by the variance calculation section 214, and the display control section 218 that performs the control process that arranges the plurality of scatter diagrams generated by combining each element based on the priority level that has been set to each element by the priority level setting section 216, and displays the plurality of scatter diagrams on the display section 122. Since the scatter diagram display device 200 sets the priority level to each element based on the variance of each scatter diagram, and arranges the scatter diagrams based on the priority level, it is possible to determine (find) the scatter diagram generated by combining characteristic elements that reflect the correlation between the elements included in the specimen S (i.e., the scatter diagram to which the greatest attention should be paid during phase analysis), and place the scatter diagram at a position (i.e., the corner of the scatter diagram matrix) at which the correlation between the elements can be easily determined. Therefore, the scatter diagram display device 200 can display a plurality of scatter diagrams (scatter diagram matrix) so that the correlation between the elements can be easily determined. For example, the scatter diagram display device 200 can automatically display a plurality of scatter diagrams (scatter diagram matrix) so that the correlation between the elements can be easily determined.

The display control section 218 included in the scatter diagram display device 200 arranges a plurality of scatter diagrams in a matrix based on the priority level that has been set to each element by the priority level setting section 216 to generate the scatter diagram matrix, and places the scatter diagram generated by combining the element to which the highest priority level has been set with the element to which the second highest priority level has been set at the corner of the scatter diagram matrix. When the user observes the scatter diagram matrix that is displayed on the display, it is considered that the user initially sees the origin (corner) of the scatter diagram matrix to check the scatter diagram situated at the corner of the scatter diagram matrix, and then moves the line of sight in the horizontal direction or the vertical direction. Therefore, when the scatter diagram to which the greatest attention should be paid is placed at the corner of the scatter diagram matrix, the user can determine the most important combination of elements at the first glance. When the name of each element included in the scatter diagram matrix is displayed as illustrated in FIG. 13, the name of the element that corresponds to the vertical axis and the name of the element that corresponds to the horizontal axis are displayed in the vicinity of only the scatter diagram that is situated at the corner of the scatter diagram matrix. Therefore, the user can immediately determine the two elements represented by the scatter diagram which is situated at the corner of the scatter diagram matrix and to which the greatest attention should be paid.

The scatter diagram display method that is implemented by the scatter diagram display device 200 includes a scatter diagram generation step that generates a plurality of scatter diagrams by combining each element based on the intensity or concentration map data that represents each element (step S22), a variance calculation step that calculates the variance of each scatter diagram generated by the scatter diagram generation step (step S24), a priority level setting step that sets the priority level to each element based on the variance of each scatter diagram calculated by the variance calculation step (step S26), and a display control step that performs the control process that arranges the plurality of scatter diagrams generated by combining each element based on the priority level that has been set to each element by the priority level setting step, and displays the plurality of scatter diagrams on the display section 122 (step S28). Since the scatter diagram display method sets the priority level to each element based on the variance of each scatter diagram, and arranges the scatter diagrams based on the priority level, it is possible to determine (find) the scatter diagram generated by combining characteristic elements that reflect the correlation between the elements included in the specimen S (i.e., the scatter diagram to which the greatest attention should be paid during phase analysis), and place the scatter diagram at a position (i.e., the corner of the scatter diagram matrix) at which the correlation between the elements can be easily determined. Therefore, the scatter diagram display method can display a plurality of scatter diagrams (scatter diagram matrix) so that the correlation between the elements can be easily determined.

Since the surface analyzer 2000 includes the scatter diagram display device 200, the surface analyzer 2000 can display a plurality of scatter diagrams (scatter diagram matrix) so that the correlation between the elements can be easily determined.

The invention is not limited to the above embodiments. Various modifications and variations may be made without departing from the scope of the invention.

The scatter diagram display device 100 according to the first embodiment has been described above taking an example in which the priority level setting section 116 sets the highest priority level to an element for which the principal component coefficient of the first principal component has the largest absolute value, and sets the second highest priority level to an element for which the principal component coefficient of the second principal component has the largest absolute value. Note that the scatter diagram display device may be configured so that the highest priority level is set to an element for which the principal component coefficient of the first principal component has the largest absolute value, and the second highest priority level is set to an element for which the principal component coefficient of the first principal component has the second largest absolute value. In this case, a plurality of scatter diagrams (scatter diagram matrix) can also be displayed so that the correlation between the elements can be easily determined.

Although the first embodiment and the second embodiment have been described taking an example in which the surface analyzer (1000, 2000) is an electron probe microanalyzer (EPMA), the surface analyzer is not particularly limited as long as the surface analyzer is a device that can acquire elemental map data. For example, the surface analyzer may be a scanning transmission electron microscope (SEM) that is provided with an Auger electron spectroscope, an X-ray photoelectron spectroscope (XPS), an energy dispersive X-ray spectrometer (EDS), or the like.

Although the first embodiment has been described taking an example in which the scatter diagram display device 100 is included in the surface analyzer 1000, and the second embodiment has been described taking an example in which the scatter diagram display device 200 is included in the surface analyzer 2000, the scatter diagram display device need not necessarily be included in the surface analyzer. For example, the scatter diagram display device may acquire the elemental map data through the information storage medium 126, and display the scatter diagram (see above).

The invention includes various other configurations substantially the same as the configurations described above in connection with the first embodiment and the second embodiment (e.g., a configuration having the same function, method, and results, or a configuration having the same objective and effects). The invention also includes a configuration in which an unsubstantial element described above in connection with the first embodiment and the second embodiment is replaced by another element. The invention also includes a configuration having the same effects as those of the configurations described above in connection with the first embodiment and the second embodiment, or a configuration capable of achieving the same objective as that of the configurations described above in connection with the first embodiment and the second embodiment. The invention further includes a configuration in which a known technique is added to the configurations described in connection with the first embodiment and the second embodiment.

Although only some embodiments of the invention have been described in detail above, those skilled in the art would readily appreciate that many modifications are possible in the embodiments without materially departing from the novel teachings and advantages of the invention. Accordingly, all such modifications are intended to be included within the scope of the invention.

What is claimed is:

1. A scatter diagram display device comprising:
   a principal component analysis section that performs principal component analysis on n pieces (n is a natural number equal to or more than 3) of element map data that represents distribution of intensity or concentration of n elements, and calculates a principal component coefficient of a second principal component for each of the n elements;

a priority level setting section that sets a priority level to each of the n elements based on the magnitudes of the principal component coefficient of the first principal component and the principal component coefficient of a second principal component, or based on the magnitude of the principal component coefficient of the first principal component obtained by the principal component analysis performed by the principal component analysis section; and a display control section that performs a control process that arranges n×(n−1)/2 scatter diagrams generated by combining two different elements from among the n pieces of element map data in a matrix based on the priority level that has been set to each element by the priority level setting section to generate a scatter diagram matrix, and displays the scatter diagram matrix on a display section, the display control section performing a control process that places a scatter diagram generated by combining one of the n elements having a highest priority level with another one of the n elements having a second highest priority level at a corner of the scatter diagram matrix, the display control section performing a control process that arranges (n−2) scatter diagram generated by combining the element having the highest priority level with another one of the n elements having a third highest or succeeding priority level in a vertical direction from the corner of the scatter diagram matrix in descending order of the third highest or succeeding priority level, and the display control section performing a control process that arranges (n−2) scatter diagrams generated by combining the element having the second highest priority level with the element having the third highest or succeeding priority level in a horizontal direction toward the corner of the scatter diagram matrix in descending order of the third highest or succeeding priority level.

2. The scatter diagram display device as defined in claim 1,
wherein the priority level setting section sets the highest priority level to an element for which the principal component coefficient of the first principal component has a largest absolute value, and sets the second highest priority level to an element for which a principal component coefficient of the second principal component has a largest absolute value.

3. The scatter diagram display device as defined in claim 1,
wherein the priority level setting section sets the highest priority level to an element for which the principal component coefficient of the first principal component has a largest absolute value, and sets the second highest priority level to an element for which the principal component coefficient of the first principal component has a second largest absolute value.

4. A scatter diagram display device comprising:
a scatter diagram generation section that generates n×(n−1)/2 a plurality of scatter diagrams (n is a natural number equal to or more than 3) by combining two different elements from among n pieces of element map data that represents distribution of intensity or concentration of n elements;

a variance calculation section that calculates variance of each of the n (n−1)/2 scatter diagrams generated by the scatter diagram generation section;

a priority level setting section that sets a priority level to each of the n elements based on the magnitude of the variance of each of the n×(n−1)/2 scatter diagrams calculated by the variance calculation section; and a display control section that performs a control process that arranges the n×(n−1)/2 scatter diagrams in a matrix based on the priority level that has been set to each of the n elements by the priority level setting section to generate a scatter diagram matrix, and displays the scatter diagram matrix on a display section, the display control section performing a control process that places a scatter diagram generated by combining one of the n elements having a highest priority level with another one of the n elements having a second highest priority level at a corner of the scatter diagram matrix, the display control section performing a control process that arranges (n−2) scatter diagrams generated by combining the element having the second highest priority level with another one of the n elements having the third highest or succeeding priority level in a vertical direction from the corner of the scatter diagram matrix in descending order of the third highest or succeeding priority level, and the display control section performing a control process that arranges (n−2) scatter diagrams generated by combining the element having the second highest priority level with the element having the third highest or succeeding priority level in a horizontal direction toward the corner of the scatter diagram matrix in descending order of the third highest or succeeding priority level.

5. A surface analyzer comprising the scatter diagram display device as defined in claim 1.

* * * * *

UNITED STATES PATENT AND TRADEMARK OFFICE
CERTIFICATE OF CORRECTION

PATENT NO. : 9,874,532 B2
APPLICATION NO. : 14/886345
DATED : January 23, 2018
INVENTOR(S) : Norihisa Mori et al.

Page 1 of 1

It is certified that error appears in the above-identified patent and that said Letters Patent is hereby corrected as shown below:

Column 22, Line 12, Claim 4, before "scatter" delete "a plurality of"

Column 22, Line 17, Claim 4, delete "n (n-1)/2" and insert -- n × (n-1)/2 --

Signed and Sealed this
Seventeenth Day of April, 2018

Andrei Iancu
*Director of the United States Patent and Trademark Office*